(12) United States Patent
Romero (10) Patent No.: US 8,784,418 B2
(45) Date of Patent: Jul. 22, 2014

(54) ENDOSCOPIC SURGICAL FORCEPS (75) Inventor: Paul R. Romero, Loveland, CO (US)

(73) Assignee: Covidien LP, Mansfield, MA (US)

( * ) Notice: Subject to any disclaimer, the term of this patent is extended or adjusted under 35 U.S.C. 154(b) by 869 days.

(21) Appl. No.: 12/955,010

(22) Filed: Nov. 29, 2010

(65) Prior Publication Data
US 2012/0136353 A1   May 31, 2012

(51) Int. Cl.
A61B 18/00   (2006.01)
(52) U.S. Cl.
USPC ................ 606/52; 606/51; 606/206; 606/207
(58) Field of Classification Search
CPC ............ A61B 18/085; A61B 18/1442; A61B 18/1445; A61B 18/1447; A61B 2017/2901–2017/2906; A61B 2017/2908; A61B 2018/0225
USPC ...................................... 606/51–52, 205–207
See application file for complete search history.

(56) References Cited

U.S. PATENT DOCUMENTS

| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,411,519 A | 5/1995 | Tovey et al. |
| 5,462,546 A * | 10/1995 | Rydell ............................. 606/51 |
| 5,649,957 A * | 7/1997 | Levin ............................. 606/207 |
| D384,413 S | 9/1997 | Zlock et al. |
| D402,028 S | 12/1998 | Grimm et al. |
| D416,089 S | 11/1999 | Barton et al. |
| D424,694 S | 5/2000 | Tetzlaff et al. |
| D425,201 S | 5/2000 | Tetzlaff et al. |

(Continued)

FOREIGN PATENT DOCUMENTS

| DE | 2415263 | 10/1975 |
| DE | 2514501 | 10/1976 |

(Continued)

OTHER PUBLICATIONS

U.S. Appl. No. 08/926,869, filed Sep. 10, 1997, James G. Chandler.

(Continued)

Primary Examiner — Michael Peffley
Assistant Examiner — Khadijeh Vahdat (57) ABSTRACT An end effector assembly for an endoscopic surgical instrument includes a pair of jaw members disposed in opposing relation relative to one another. One or both of the jaw members is moveable relative to the other between a spaced-apart position and an approximated position for grasping tissue therebetween. Each jaw member defines an arcuate configuration and includes a proximal segment and a distal segment coupled to the proximal segment. The distal segment is moveable with respect to the proximal segment between a use position, wherein the proximal segment and the distal segment cooperate to define the arcuate configuration of the jaw member, and an insertion position, wherein the distal segment is offset relative to the proximal segment to interrupt the arcuate configuration of the jaw member.

9 Claims, 5 Drawing Sheets

(56) References Cited

U.S. PATENT DOCUMENTS

| | | |
|---|---|---|
| D449,886 S | 10/2001 | Tetzlaff et al. |
| D454,951 S | 3/2002 | Bon |
| D457,958 S | 5/2002 | Dycus et al. |
| D457,959 S | 5/2002 | Tetzlaff et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,651,017 B2 | 1/2010 | Ortiz et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 19738457 | 1/2009 |
| DE | 10 2008 018406 | 7/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 6-285078 | 10/1994 |
| JP | 6-511401 | 12/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| JP | 2001-190564 | 7/2001 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/576,380, filed Oct. 9, 2009, Wayne Siebrecht.
U.S. Appl. No. 12/607,191, filed Oct. 28, 2009, William H. Nau Jr.
U.S. Appl. No. 12/619,100, filed Nov. 16, 2009, Jennifer S. Harper.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Horner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.

(56) References Cited

OTHER PUBLICATIONS

U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/004,984, filed Jan. 12, 2011, David M. Garrison.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/048,679, filed Mar. 15, 2011, Paul Guerra.
U.S. Appl. No. 13/075,847, filed Mar. 30, 2011, Gary M. Couture.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.

(56) References Cited

OTHER PUBLICATIONS

Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181969.6 dated Feb. 4, 2011.
Int'l Search Report EP 10 191320.0 dated Feb. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

\* cited by examiner

ENDOSCOPIC SURGICAL FORCEPS

BACKGROUND

The present disclosure relates to surgical instruments. More particularly, the present disclosure relates to endoscopic surgical forceps for sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Typically, after a vessel or tissue is sealed, the surgeon advances a knife to sever the sealed tissue disposed between the opposing jaw members.

SUMMARY

The present disclosure relates to an end effector assembly for an endoscopic surgical instrument. The end effector assembly includes a pair of jaw members disposed in opposing relation relative to one another. One or both of the jaw members is moveable relative to the other between a spaced-apart position and an approximated position for grasping tissue therebetween. Each jaw member defines an arcuate configuration and includes a proximal segment and a distal segment. The distal segment is coupled to the proximal segment and is moveable with respect to the proximal segment between a use position and an insertion position. In the use position, the proximal segment and the distal segment cooperate to define the arcuate configuration of the jaw member. In the insertion position, on the other hand, the distal segment is offset relative to the proximal segment to interrupt the arcuate configuration of the jaw member.

In one embodiment, each jaw member includes an opposed electrically conductive tissue sealing surface. One or both of the tissue sealing surfaces may be adapted to connect to a source of electrosurgical energy for conducting energy through tissue grasped between the jaw members. Further, the tissue sealing surface of each jaw member may include a proximal portion disposed on the proximal segment of the jaw member and a distal portion disposed on the distal segment of the jaw member.

In another embodiment, the distal segment of each jaw member is biased toward the use position. Further, a locking mechanism may be provided for locking the distal segment of each of the jaw members in the insertion position.

In still another embodiment, the distal segment of each jaw member is pivotably coupled to the proximal segment of the respective jaw member. In such an embodiment, the distal segment is rotatable with respect to the proximal segment between the use position and the insertion position.

In yet another embodiment, the end effector assembly defines a first overall width when the distal segments of the jaw members are disposed in the use position and a second overall width when the distal segments of the jaw members are disposed in the insertion position. The second overall width is smaller than the first overall width such that, when the distal segments of the jaw members are in the insertion position, the end effector assembly may be inserted into an internal surgical site, e.g., through a cannula assembly.

In still yet another embodiment, the distal segment and/or the proximal segment of each jaw member includes a clearance feature configured to permit movement of the distal segment with respect to the proximal segment from the use position to the insertion position.

In accordance with another embodiment of the present disclosure, an end effector assembly for an endoscopic surgical instrument is provided. The end effector assembly includes first and second jaw members disposed in opposing relation relative to one another and moveable with respect to one another between a spaced-apart position and an approximated position for grasping tissue therebetween. Each jaw member includes a proximal segment and a distal segment pivotably coupled to the proximal segment. The distal segment is moveable with respect to the proximal segment between a use position and an insertion position. Each jaw member further includes an opposed electrically conductive tissue sealing surface. Each sealing surface includes a proximal portion disposed on the proximal segment of the jaw member and a distal portion disposed on the distal segment of the jaw member. In the use position, the proximal and distal portions of the sealing surface cooperate to define an arcuate configuration. In the insertion position, on the other hand, the distal portion of the sealing surface is offset from the proximal portion of the sealing surface to interrupt the arcuate configuration of the sealing surface.

As in the previous embodiment, the distal segments of the jaw members may be biased toward the use position. Further, the distal segment of each jaw member may be pivotably coupled to the proximal segments of the respective jaw members such that the distal segment is rotatable with respect to the proximal segment between the use position and the insertion position. A locking mechanism may also be provided for locking the distal segment of each of the jaw members in the insertion position.

In another embodiment, the end effector assembly defines a first width when disposed in the use position and a second width when disposed in the insertion position, the second width being less than the first width.

In yet another embodiment, one or both of the distal segment and the proximal segment of each jaw member includes a clearance feature configured to permit movement of the distal segment with respect to the proximal segment from the use position to the insertion position.

BRIEF DESCRIPTION OF THE DRAWINGS

Various embodiments of the presently disclosed forceps are described herein with reference to the drawings, wherein.

DETAILED DESCRIPTION

Embodiments of the presently disclosed surgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 1:
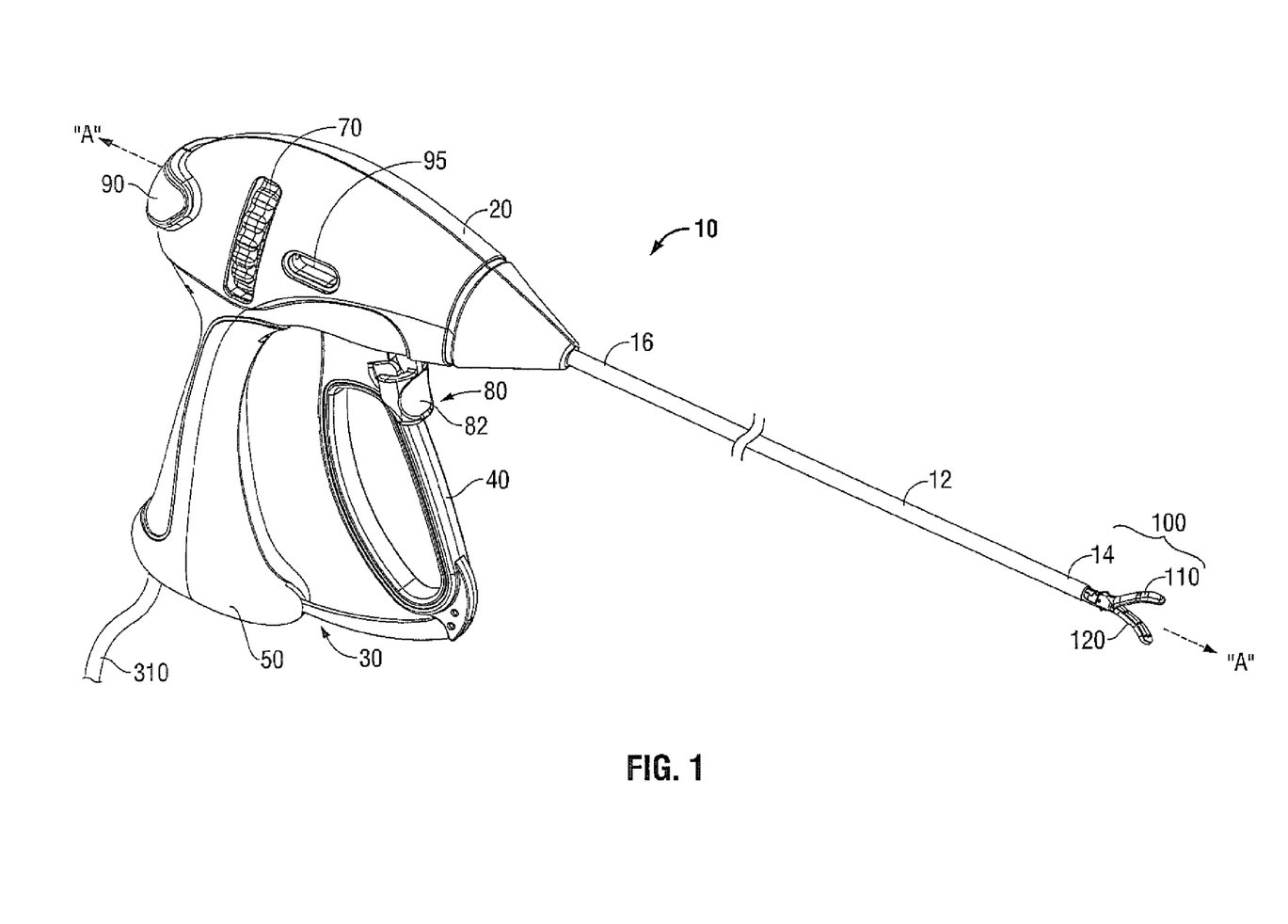
FIG. 1 is a perspective view of an endoscopic forceps having an end effector assembly in accordance with an embodiment of the present disclosure.

Turning now to FIG. 1, a forceps 10 is provided defining a longitudinal axis "A-A" and including a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 310 that connects forceps 10 to a generator (not shown) or other suitable power source, although forceps 10 may alternatively be configured as a battery powered instrument. Cable 310 includes a wire (not explicitly shown) disposed therein that has sufficient length to extend through shaft 12 in order to provide electrical energy to at least one of the jaw members 110 and 120 of end effector assembly 100.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about a longitudinal axis "A-A" to rotate end effector 100 about longitudinal axis "A-A." The housing 20 houses the internal working components of the forceps 10.

Figure 3:
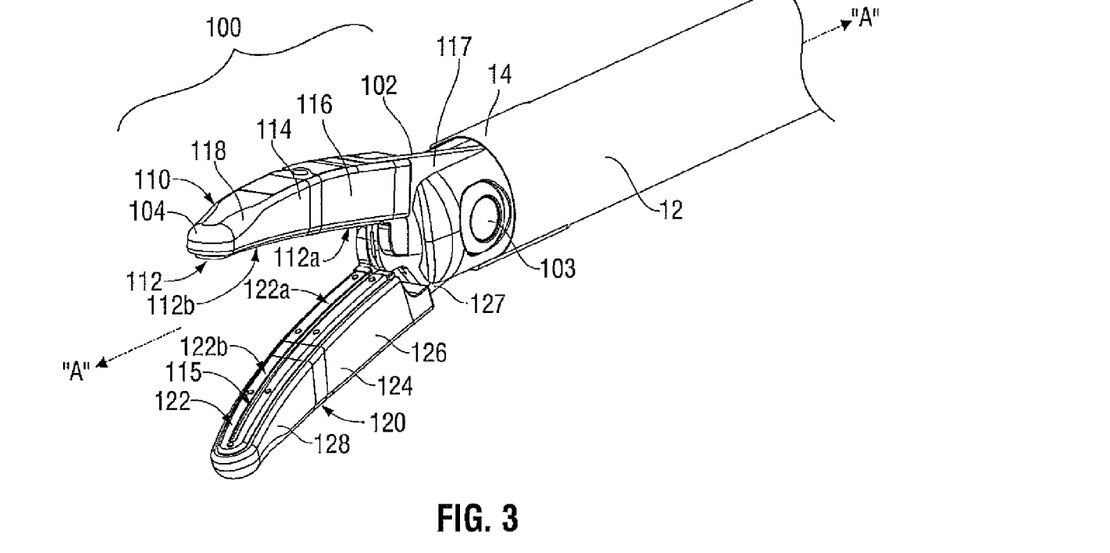
FIG. 3 is an enlarged, perspective view of an end effector assembly for use with the forceps of FIG. 1 wherein jaw members of the end effector assembly are disposed in a spaced-apart position.
Figure 4:
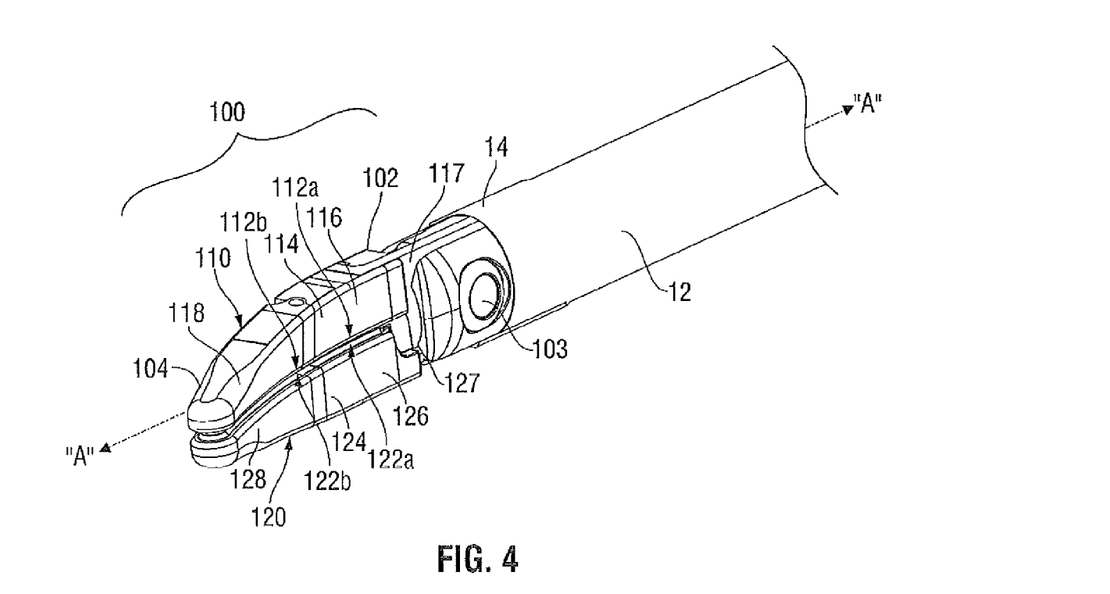
FIG. 4 is an enlarged, perspective view of the end effector assembly for use with the forceps of FIG. 1 wherein jaw members of the end effector assembly are disposed in an approximated position.

Referring momentarily to FIGS. 3-4, end effector assembly 100 is shown attached at a distal end 14 of shaft 12 and includes a pair of opposing jaw members 110 and 120. Each of jaw members 110 and 120 includes an opposed electrically conductive tissue sealing surface 112 and 122, respectively. End effector assembly 100 is designed as a bilateral assembly, i.e., both jaw member 110 and jaw member 120 are moveable about a pivot 103 relative to one another and to the shaft 12. However, end effector assembly 100 may alternatively be configured as a unilateral assembly, i.e., where one of the jaw members 110, 120 is fixed relative to shaft 12 and the other jaw member 110, 120 is moveable about pivot 103 relative to shaft 12 and the fixed jaw member 110, 120. In some embodiments, a knife assembly (not shown) is disposed within shaft 12 and a knife channel 115 (FIG. 3) is defined within one or both jaw members 110, 120 to permit reciprocation of a knife blade (not shown) therethrough.

Referring back to FIG. 1, moveable handle 40 of handle assembly 30 is ultimately connected to a drive assembly (not shown) that, together, mechanically cooperate to impart movement of jaw members 110 and 120 between a spaced-apart position and an approximated position to grasp tissue disposed between sealing surfaces 112 and 122 (FIG. 3) of jaw members 110, 120, respectively. As shown in FIG. 1, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position of jaw members 110, 120.

Figure 2:
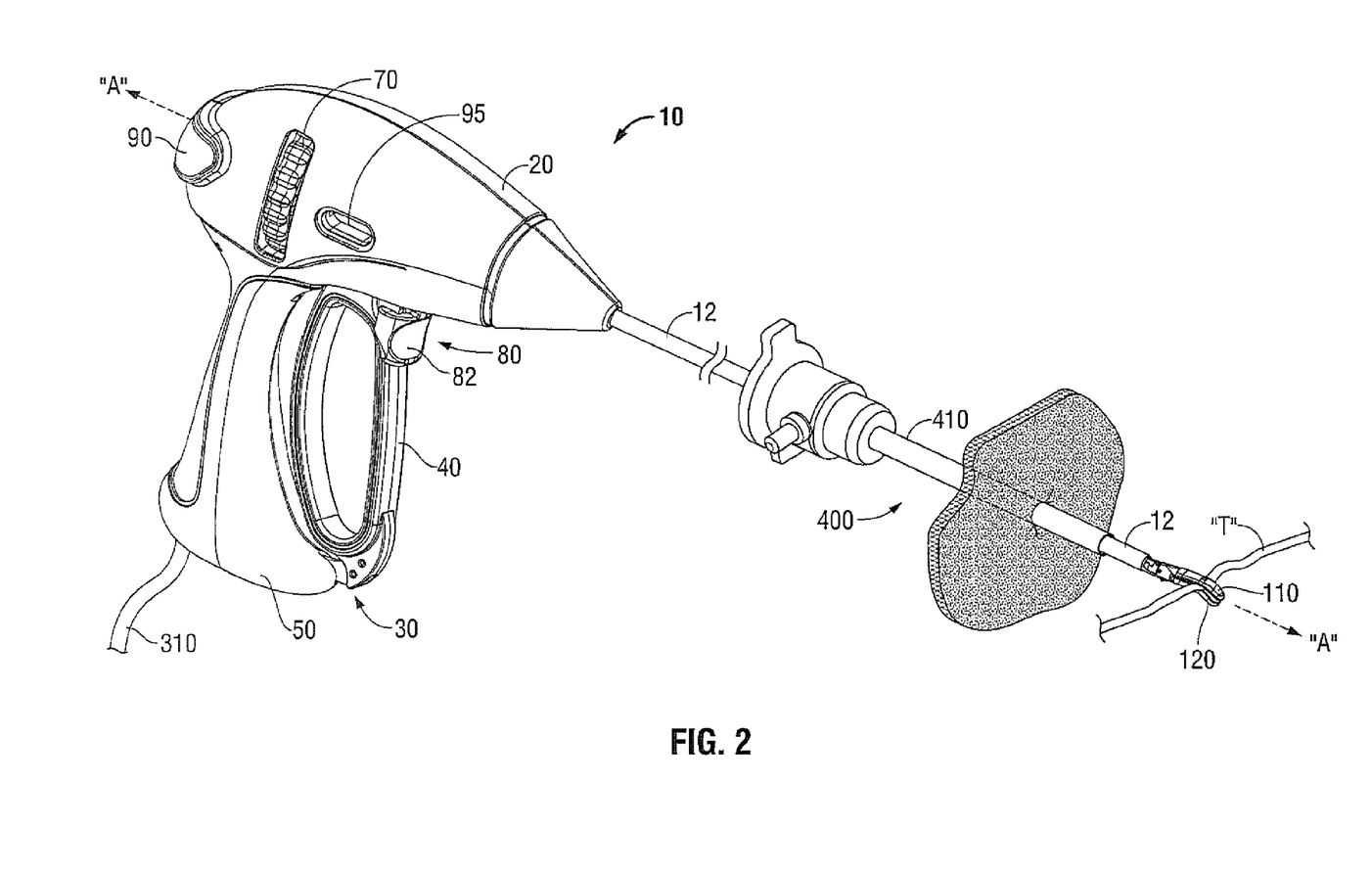
FIG. 2 is a perspective view of the forceps of FIG. 1 wherein the end effector assembly has been inserted through a cannula assembly and is positioned adjacent internal body tissue.

Turning now to FIG. 2, forceps 10 is configured as an endoscopic surgical instrument. More particularly, end effector assembly 100 and shaft 12 are configured for insertion through a cannula assembly 400 for positioning adjacent an internal surgical site, e.g., for grasping, sealing and/or dividing tissue "T" during a minimally-invasive surgical procedure. As can be appreciated, end effector assembly 100 and shaft 12 are constrained by the internal dimensions of elongated tubular member 410 of cannula assembly 400. As will be described in greater detail below, jaw members 110, 120 of end effector assembly 100 are moveable between a use position (FIG. 6), wherein jaw members 110, 120 are operable to grasp, seal and/or divide tissue, and an insertion position (FIG. 7), wherein the overall width of end effector assembly 100 is reduced to permit insertion of end effector assembly 100 through elongated tubular member 410 of cannula assembly 400 and into position adjacent tissue "T" to be grasped, sealed and/or divided.

Referring once again to FIGS. 3-4, each jaw member 110, 120 defines an arcuate configuration, curving laterally relative to longitudinal axis "A-A" from the proximal end 102 to the distal end 104 thereof. The degree of curvature of jaw members 110, 120 may be configured according to the particular surgical procedure to be performed, the size and/or composition of tissue to be grasped, sealed and/or divided, or based upon other factors. However, as will be described below, the curvature of jaw members 110, 120 is not significantly limited by the spatial constraints of cannula assembly 400 (FIG. 2), since jaw members 110, 120 are capable of moving between a use position (FIGS. 3-4 and 6), wherein the full curvature of jaw members 110, 120 is realized, and an insertion position (FIG. 7), wherein the outer dimensions, e.g., the width, of end effector assembly 100 is reduced to permit insertion of end effector assembly 100 through cannula assembly 400 (FIG. 2).

With continued reference to FIGS. 3-4, jaw members 110, 120 each include a jaw housing 114, 124, respectively, and an opposed electrically conductive tissue sealing surface 112, 122, respectively. As mentioned above, a wire, or wires (not shown), disposed within cable 310 (FIG. 1) may extend through shaft 12 and into either or both jaw housings 114, 124 of jaw members 110, 120, respectively, ultimately coupling the source of electrosurgical energy (not shown) to sealing surface 112 and/or sealing surface 122 of jaw members 110, 120, respectively. Further, each jaw member 110, 120 includes a proximal segment 116, 126, respectively, and a distal segment 118, 128, respectively. Proximal segments 116, 126 of jaw members 110, 120, respectively, are fixedly engaged at proximal ends thereof to flanges 117, 127, respectively. Flanges 117, 127 of jaw members 110, 120, respectively, are pivotably engaged to one another via pivot 103 to permit jaw members 110, 120 to move between the spaced-apart position (FIG. 3) and the approximated position (FIG. 4). Distal segments 118, 128 of jaw members 110, 120, respectively, abut proximal segments 116, 126, respectively, of jaw members 110, 120 and are pivotably coupled to proximal segments 116, 126, respectively. Sealing surfaces 112, 122 of jaw members 110, 120, respectively, are similarly divided into proximal portions 112a, 122a, disposed on respective proximal segments 116, 126 of jaw members 110, 120, and distal portions 112b, 122b, disposed on respective distal segments 118, 128, of jaw members 110, 120.

Figure 5A:
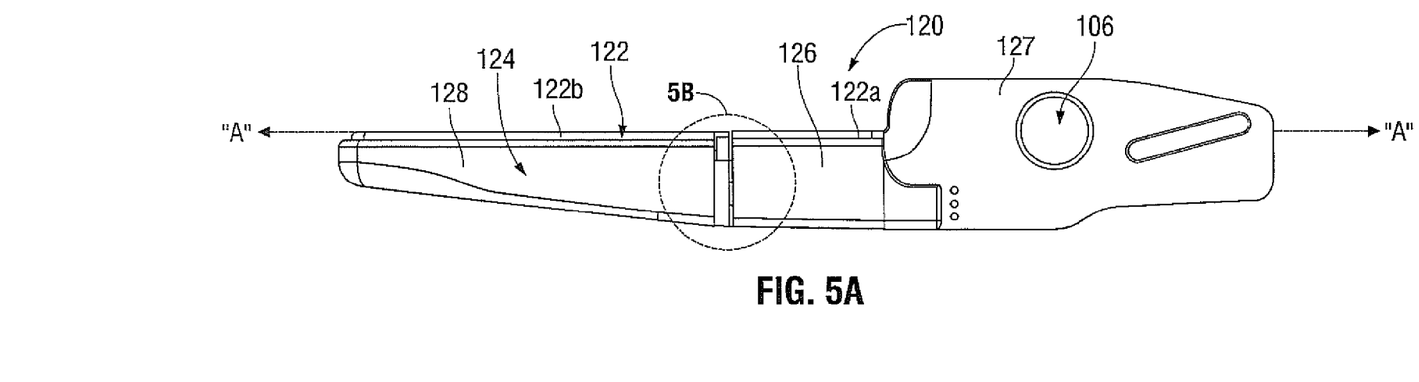
FIG. 5A is an isolated, side view of one jaw member of the end effector assembly of FIGS. 3-4.
Figure 5B:
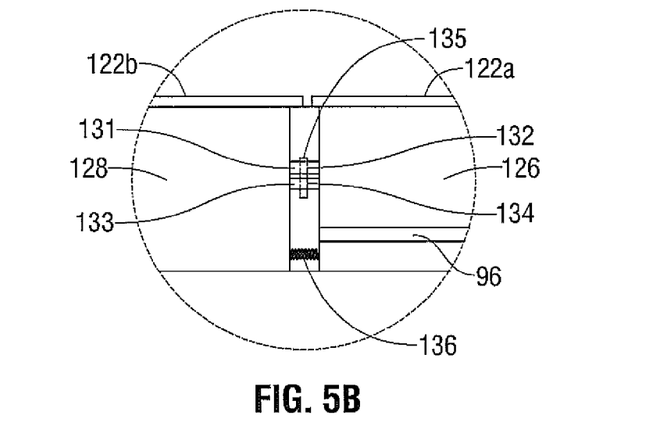
FIG. 5B is a greatly enlarged, side view of the area of detail of FIG. 5A.
Figure 6:
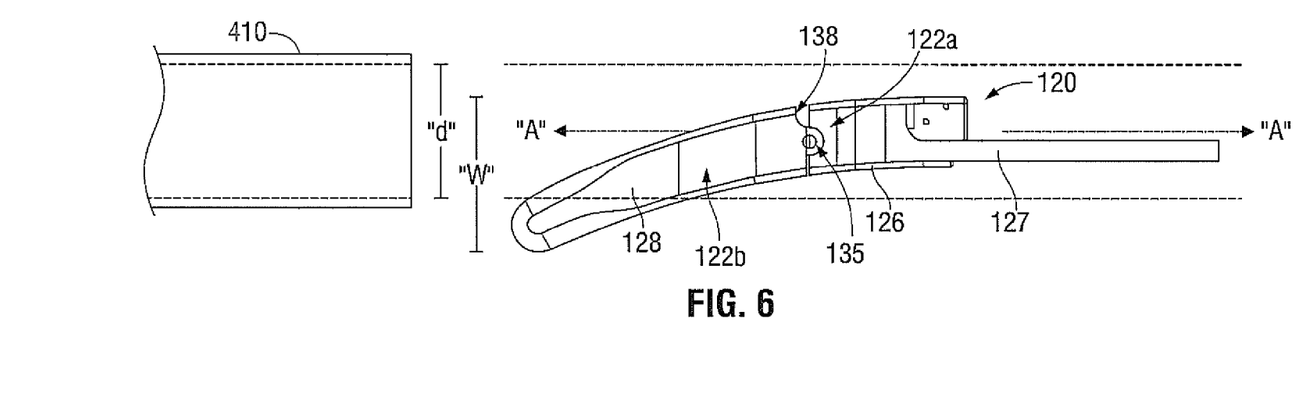
FIG. 6 is an isolated, top view of the jaw member of FIG. 5 shown disposed in a use position.
Figure 7:
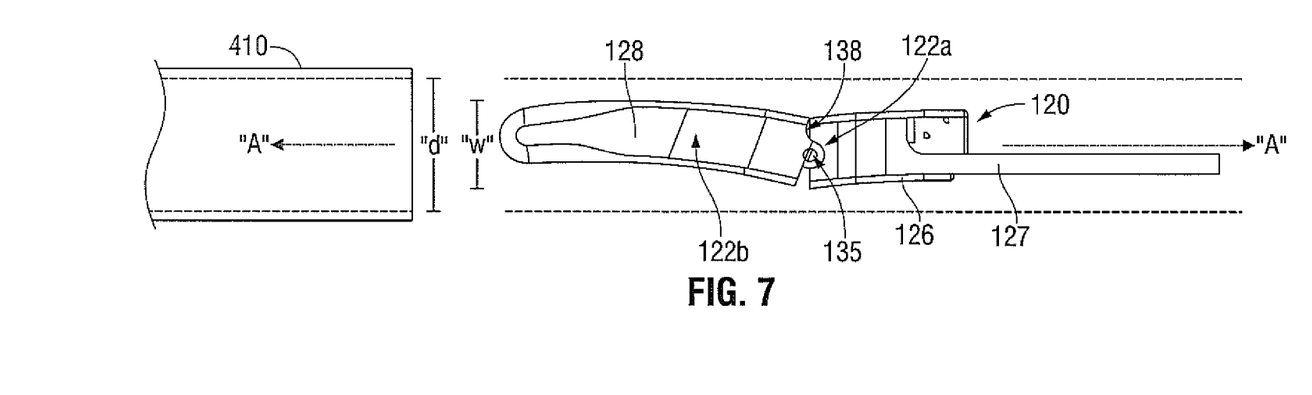
FIG. 7 is an isolated, top view of the jaw member of FIG. 5 shown disposed in an insertion position.

Turning now to FIGS. 5A-7, jaw member 120 is shown moving between the use position (FIG. 6) and the insertion position (FIG. 7). Although not shown in FIGS. 5A-7, jaw member 110 is configured similarly to jaw member 120 and, thus, will not be described herein to avoid unnecessary repetition.

As shown in FIGS. 5A-6, and as mentioned above, jaw member 120 includes a proximally-extending flange 127, a proximal segment 126, and a distal segment 128. Flange 127 includes an aperture 106 defined therethrough that is configured to accept pivot pin 103 (FIG. 3) for pivotably engaging jaw members 110, 120 to one another. Proximal and distal segments 126, 128 of jaw member 120 and corresponding proximal and distal portions 122a, 122b, respectively, of sealing surface 122, cooperate with one another to fully form a substantially continuous jaw member 120 and a substantially continuous sealing surface 122 when disposed in the use position (FIGS. 5A-6). In other words, as best shown in FIG. 6, when in the use position, proximal and distal segments 126, 128, respectively, of jaw member 120 and proximal and distal potions, 122a, 122b, respectively, of jaw member 120 abut one another in an aligned relationship such that jaw member 120 defines an arcuate configuration curving laterally relative to longitudinal axis "A-A." Further, when in the use position, proximal and distal portions 122a, 122b of electrically-conductive tissue sealing surface 122 are in contact with one another (or are otherwise electrically coupled to one another) such that, with tissue "T" (FIG. 2) grasped between jaw members 110, 120, a tissue seal may be effected along the entire length of sealing surfaces 112, 122, e.g., along both the proximal and distal portions 122a, 122b of sealing surface 122 and similarly with respect to sealing surface 112.

As mentioned above, proximal and distal segments 126, 128 of jaw member 120 are pivotably coupled to one another. More particularly, distal segment 128 of jaw member 120 includes a semi-circular tab 131 extending proximally therefrom and defining an aperture 132 therethrough. Proximal segment 126 of jaw member 120 similarly includes a semi-circular tab 133 extending distally therefrom and defining an aperture 134 therethrough. Tabs 131, 133 of distal and proximal segments 128, 126, respectively, are disposed in an overlapping configuration with respect to one another such that the apertures 132, 134 thereof are in alignment. A pivot pin 135 is engaged within apertures 132, 134 of distal and proximal segments 128, 126 to pivotably couple proximal and distal segments 126, 128 to one another. Alternatively, proximal and distal segments 126, 128 may be pivotably coupled to one another in any other suitable fashion.

Pivot pin 135 may be centered on longitudinal axis "A-A," or may be offset relative to longitudinal axis "A-A." For example, in embodiments where a knife assembly (not shown) is disposed within shaft 12 (FIG. 3) and a knife channel 115 (FIG. 3) is defined within jaw members 110, 120, pivot pin 135 may be offset laterally with respect to longitudinal axis "A-A" to permit the knife blade (not shown) to reciprocate substantially completely through knife channel 115 (FIG. 3). Alternatively, pivot pin 135 may be offset vertically with respect to longitudinal axis "A-A," e.g., pivot pin 135 may be disposed within jaw housing 124 further from sealing surface 122, to permit the knife blade (not shown) to pass through knife channel 115 above pivot pin 135.

With continued reference to FIGS. 5A, 5B and 6, distal segment 128 of jaw member 120 may be biased toward the use position. More specifically, a biasing member 136, e.g., a compression spring or an extension spring, may be disposed between abutting surfaces of proximal and distal segments 126, 128, respectively, of jaw member 120 to retain jaw member 120 in the use position when at-rest. Alternatively, pivot pin 135 may include a torsional spring or other torsion biasing member (not shown) for retaining jaw member 120 in the use position when at-rest. Additionally, or alternatively, as will be described below, a locking mechanism may be provided for releasably locking jaw member 120 in the use position and/or the insertion position. Further, feedback features (not shown) may be provided to indicate to the surgeon the position of jaw member 120, e.g., whether jaw member 120 is in the use position (FIG. 6) or the insertion position (FIG. 7).

In operation, as shown in FIGS. 2-4, with proximal and distal segments 116, 126, and 118, 128, respectively, of respective jaw members 110, 120 disposed in the use position, end effector assembly 100 may be positioned adjacent tissue "T" to be grasped, sealed and/or divided. More particularly, with jaw members 110, 120 in the spaced-apart position (FIG. 3), end effector assembly 100 may be positioned such that tissue "T" is disposed between sealing surfaces 112, 122 of jaw members 110, 120, respectively. Thereafter, jaw members 110, 120 may be moved to the approximated position (FIG. 4), e.g., via depressing moveable handle 40, to grasp tissue "T" between sealing surfaces 112, 122. Next, via activation of actuator 90, electrosurgical energy may be supplied to sealing surfaces 112, 122 of jaw members 110, 120, respectively, and conducted through tissue "T" to effect a tissue seal. After the sealing operation is complete, trigger 82 may be actuated to advance the knife blade (not shown) between jaw members 110, 120 to cut tissue along the previously-formed tissue seal.

Throughout the above-described operation of end effector assembly 100, proximal and distal segments 116, 126, and 118, 128, respectively, of respective jaw members 110, 120 are maintained in the use position due the bias toward the use position and/or are locked in the use position via a locking mechanism (not shown). In this use position, due to the arcuate configuration of jaw members 110, 120, end effector assembly 100 defines a width "W" that is greater than a diameter "d" of elongated tubular member 410 of cannula assembly 400 (see FIG. 6). As such, although the above-described arcuate configuration of jaw members 110, 120 is desirable for the use and operation of end effector assembly 100, the spatial constraints of minimally-invasive surgical procedures make it is necessary to transition jaw members 110, 120 from the use position to the insertion position to permit end effector assembly 100 to be inserted into and removed from an internal surgical site via cannula assembly 400.

Turning now to FIG. 7, jaw member 120 is shown in the insertion position. Jaw member 110 operates in a similar fashion but is not described for purposed of brevity. As mentioned above, end effector assembly 100 is both inserted and removed from cannula assembly 400 in this insertion position. In the insertion position, distal segment 128 of jaw member 120 is rotated about pivot pin 135, against the bias of biasing member 136, such that jaw member 120 no longer forms an arcuate configuration but, rather, forms an interrupted, or disjointed configuration. More particularly, jaw member 120 is pivoted in an opposite direction relative to the direction of curvature of jaw member 120 when in the use position such that the pivoting of jaw member 120 at least partially compensates for the curvature of jaw member 120, thereby reducing the overall width of jaw member 120 to a width "w" that is smaller than both the width "W" of jaw member 120 in the use position and the diameter "d" of elongated tubular member 410 of cannula assembly 400.

As can be appreciated, the degree of rotation of distal segment 128 of jaw member 120 from the use position to the insertion position may depend on the overall degree of curvature of jaw member 120 and/or the overall configuration of end effector assembly 100 relative to cannula assembly 400. As such, where the degree of curvature of jaw member 120 is relatively large, distal segment 128 of jaw member 120 may be rotated through a relatively large angle with respect to proximal portion 126 of jaw member 120. On the other hand, where jaw member 120 is curved a relatively small degree, it may only be necessary to rotate distal segment 128 of jaw member 120 though a small angle relative to proximal portion 126 of jaw member 120. Further, pivot pin 135 may be moved further proximally or distally along jaw member 120 in order to accommodate greater or smaller degrees of curvature of jaw member 120.

With continued reference to FIG. 7, distal segment 128 of jaw member 120 (and/or proximal segment 126 of jaw member 120) may include one or more clearance features, e.g., a cut-out portion 138, to permit full rotation of distal segment 128 to the insertion position. As can be appreciated, such a feature permits distal segment 128 to rotate further with respect to proximal segment 126.

In use, distal segments 118, 128 of jaw members 110, 120, respectively, may be moved to the insertion position upon contacting elongated tubular member 410 of cannula assembly 400, e.g., when end effector assembly 100 is inserted into cannula assembly 400, the inner surface of elongated tubular member 410 may urge distal segments 118, 128 of jaw member 110, 120 against the bias of biasing member 136 to the insertion position to thereby permit translation of end effector assembly 100 therethrough. Similarly upon removal, the contacting of distal segments 118, 128 of jaw members 110, 120, respectively, with the inner surface of elongated tubular member 410 of cannula assembly 400 may be sufficient to overcome the bias of biasing member 136, thereby allowing end effector assembly 100 to be removed from the internal surgical site via cannula assembly 400. Alternatively, a switch 95 (or other control member) disposed on housing 20 may be provided for selectively moving distal segments 118, 128 of jaw members 110, 120, respectively, to the insertion position and/or for retaining distal segments 118, 128 in the insertion position. For example, as best shown in FIG. 5B, proximal segment 126 of jaw member 120 may include a rod 96 disposed within jaw housing 124 that is operably coupled to a switch 95 (FIG. 1) disposed on housing 20 that is configured to move between a retracted position and an extended position. When switch 95 (FIG. 1) is in an un-actuated state, rod 96 may be disposed substantially within proximal segment 126 of jaw member 120 (the retracted position). Upon actuation of switch 95, rod 96 may be extended distally from proximal segment 126, eventually contacting the abutting surface of distal segment 128 and urging distal segment 128 to rotate about pivot 135 against the bias of biasing member 136 to the insertion position as rod 95 is advanced distally to the extended position. Thereafter, switch 95 may be fixed, or locked in the actuated position such that rod 96 is fixed in the extended position and such that distal segment 128 of jaw member 120 is fixed in the insertion position.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. An end effector assembly for an endoscopic surgical instrument, the end effector assembly comprising:
   a pair of jaw members disposed in opposing relation relative to one another, at least one of the jaw members moveable relative to the other between a spaced-apart position and an approximated position for grasping tissue therebetween, each jaw member defining an arcuate configuration and including:
   a proximal segment;
   a distal segment coupled to the proximal segment and moveable with respect to the proximal segment between a use position, wherein the proximal segment and the distal segment cooperate to define the arcuate configuration of the jaw member, and an insertion position, wherein the distal segment is offset relative to the proximal segment to interrupt the arcuate configuration of the jaw member;
   a biasing member disposed between the proximal and distal segments and configured to bias the distal segment towards the use position; and
   a rod disposed within the proximal segment and moveable between a retracted position, wherein the rod is spaced-apart from the distal segment, and an extended position, wherein the rod extends from the proximal segment and into contact with the distal segment to urge the distal segment against the bias of the biasing member to the insertion position.

2. The end effector assembly according to claim 1, wherein each jaw member includes an opposed electrically conductive tissue sealing surface, at least one of the tissue sealing surfaces adapted to connect to a source of electrosurgical energy for conducting energy through tissue.

3. The end effector assembly according to claim 2, wherein the tissue sealing surface of each jaw member includes a proximal portion disposed on the proximal segment of the jaw member and a distal portion disposed on the distal segment of the jaw member.

4. The end effector assembly according to claim 1, wherein the distal segment is pivotably coupled to the proximal segment, the distal segment being rotatable with respect to the proximal segment between the use position and the insertion position.

5. The end effector assembly according to claim 1, wherein, in the use position, the end effector assembly defines a first width and wherein, in the insertion position, the end effector assembly defines a second width less than the first width.

6. The end effector assembly according to claim 1, wherein at least one of the distal segment and the proximal segment of each jaw member includes a clearance feature configured to permit movement of the distal segment with respect to the proximal segment from the use position to the insertion position.

7. An endoscopic surgical instrument comprising:
a housing having a shaft extending therefrom;
an end effector assembly disposed at a distal end of the shaft, the end effector assembly including:
first and second jaw members disposed in opposing relation relative to one another, at least one of the jaw members moveable relative to the other between a spaced-apart position and an approximated position for grasping tissue therebetween, each jaw member including:
a proximal segment;
a distal segment pivotably coupled to the proximal segment and moveable with respect to the proximal segment between a use position and an insertion position; and
an opposed electrically conductive tissue sealing surface, the sealing surface including a proximal portion disposed on the proximal segment of the jaw member and a distal portion disposed on the distal segment of the jaw member, wherein, in the use position, the proximal and distal portions of the sealing surface cooperate to define an arcuate configuration, and wherein, in the insertion position, the distal portion of the sealing surface is offset from the proximal portion of the sealing surface to interrupt the arcuate configuration of the sealing surface;
a biasing member disposed between the proximal and distal segments and configured to bias the distal segment towards the use position; and
a rod disposed within the proximal segment and moveable between a retracted position, wherein the rod is spaced-apart from the distal segment, and an extended position, wherein the rod extends from the proximal segment and into contact with the distal segment to urge the distal segment against the bias of the biasing member to the insertion position; and
an actuator disposed on the housing and operably coupled to the rod, the actuator selectively actuatable to move the rod between the retracted and extended positions.

8. The endoscopic surgical instrument according to claim 7, wherein, in the use position, the end effector assembly defines a first width and wherein, in the insertion position, the end effector assembly defines a second width less than the first width.

9. The endoscopic surgical instrument according to claim 7, wherein at least one of the distal segment and the proximal segment of each jaw member includes a clearance feature configured to permit movement of the distal segment with respect to the proximal segment from the use position to the insertion position.

* * * * *